United States Patent [19]

Spaltro et al.

[11] Patent Number: 5,490,978
[45] Date of Patent: Feb. 13, 1996

[54] BLOCK COPOLYMERS OF POLYSACCHARIDES AND POLYALKYLENE OXIDES

[75] Inventors: Suree M. Spaltro, Hackensack, N.J.; Kavssery Ananthapadmanabhan, New Windsor; Michael P. Aronson, West Nyack, both of N.Y.; Michael Frushour, Little Ferry, N.J.

[73] Assignee: Chesebrough-Pond's USA Co., Division of Conopco, Inc., Greenwich, Conn.

[21] Appl. No.: 345,286

[22] Filed: Nov. 28, 1994

Related U.S. Application Data

[63] Continuation of Ser. No. 138,167, Oct. 15, 1993, abandoned.

[51] Int. Cl.$^6$ .................................................. A61K 7/16
[52] U.S. Cl. .................. 424/49; 523/122; 252/175; 252/180; 514/54; 514/55; 514/56; 514/57; 514/58; 514/59; 514/60; 514/61; 525/54.2; 525/54.21; 525/54.24; 525/54.3; 525/54.31; 525/54.4; 525/54.42; 536/20; 536/30; 536/45; 536/46; 536/51; 536/56; 536/102; 536/103; 536/112; 536/114
[58] Field of Search .................. 424/49; 523/122; 514/54–61; 525/54.2, 54.21, 54.24, 54.3, 54.31, 54.4, 54.42; 536/20, 30, 45, 46, 51, 56, 102, 103, 112, 114; 252/175, 180

[56] References Cited

U.S. PATENT DOCUMENTS

| | | | |
|---|---|---|---|
| 3,386,932 | 6/1968 | Steinmann | 527/301 |
| 3,414,530 | 12/1968 | Zilkha et al. | 536/103 |
| 3,950,282 | 4/1976 | Gilbert et al. | 536/32 |
| 4,038,223 | 7/1977 | Pohjola et al. | 527/301 |
| 4,360,512 | 11/1982 | Vidra | 424/56 |
| 4,447,562 | 5/1984 | Ivani | 514/772.5 |
| 4,634,743 | 1/1987 | Prier | 525/462 |
| 4,663,202 | 5/1987 | Causton | 427/388.4 |
| 4,942,501 | 7/1990 | MacFarlane et al. | 361/523 |
| 5,032,387 | 7/1991 | Hill et al. | 424/49 |

FOREIGN PATENT DOCUMENTS

49/109037  2/1974  Japan.

OTHER PUBLICATIONS

Amick, R. et al. *Polymer* 1980, 21, 648–650.
Kim, S. et al. *J. Macromol. Sci.–Chem.* 1976, A10(4), 671–679.
Kim, S. et al. *J. Polym. Sci. Polym. Lett. Ed.* 1973, 11, 731–735.
Nikitin "The Chemistry of Cellulose and Wood", Israel Program for Scientific Translations, Jerusalem, 1966, pp. 62–71.
Duval, Jean Marc et al., "Synthesis and Characterization of Some Covalent Dextran–Polyoxyethyleneglycol Derivatives". *Carbohydrate Polymers*, (1991), pp. 233–242.
Klug, E. D. "Hydroxyethyl Ethers of Cellulose and Their Analytical Determination". *Method in Carbohydrate Chemistry*, 1963, Roy L. Whistler, Editor, pp. 315–317.

*Primary Examiner*—Douglas W. Robinson
*Assistant Examiner*—Kathleen Kahler Fonda
*Attorney, Agent, or Firm*—Rimma Mitelman

[57] ABSTRACT

Polysaccharides (e.g., dextran) of different molecular weights were substituted at the anomeric carbon with polyalkylene oxides of different molecular weights to give novel diblock copolymers. The copolymers inhibit bacterial aggregation. The copolymers are useful as antiplaque agents, as agents to prevent bacterial aggregation in an aqueous system or in a fermentation system.

17 Claims, No Drawings

BLOCK COPOLYMERS OF POLYSACCHARIDES AND POLYALKYLENE OXIDES

This is a continuation of Ser. No. 08/138,167, filed Oct. 15, 1993, now abandoned.

FIELD OF THE INVENTION

The present invention relates to novel block copolymers of polysaccharides and polyalkylene oxides and the use of the copolymers to prevent bacterial aggregation or coaggregation in an aqueous system or in fermentation processes.

BACKGROUND OF THE INVENTION

It is generally recognized that the development of dental plaque begins with the adhesion of bacteria to the teeth. Bacterial adhesion to tooth surfaces usually involves stereospecific interactions between cell surface binding proteins, referred to as adhesins, and cognate structures which form binding sites either in salivary pellicle, on the surfaces of other bacteria resident in plaque, or in the extracellular plaque matrix (Gibbons, R. J.; J Dent Res 68:750–760). Plaque generally consists of bacteria, bacterial end products such as polysaccharides, inorganic salts and salivary proteins. Dextrans with their predominant alpha-1,6-glycosidic linkages as appeared in the glucan structures found in a plaque matrix are known to mediate binding of oral bacteria in the oral environment. Plaque bacteria ferment dietary carbohydrates to organic acids which demineralize enamel resulting in tooth decay. *Streptococcus mutans* and *Actinomyces viscosus* are pathological bacterial species present in dental plaque and which were found to possess a high cariogenic potential. There is a continuing need for effective and commercially feasible antiplaque agents. Streptococcus Sanguis is a primary colonizer of teeth surface which allows attachment of pathological bacteria.

Polyethylene glycol grafted surfaces are known to repel proteins. Duval et al., "Synthesis and Characterization of Some Covalent Dextran-Polyethylene Glycol Derivatives", Carbohydrate Polymers 15, 233 (1991) discloses randomly substituted copolymers of polyethylene glycol and polysaccharides. Japanese Patent Application 49010937 discloses use of glycol-modified polysaccharides or salts thereof in cosmetic lotions and creams. Like Duval et al., the Japanese reference employs randomly substituted copolymers. The copolymers taught by the present invention differ from the copolymers disclosed by Duval et al. and by the Japanese reference in at least that the present copolymers are block copolymers where at least one polysaccharide block is substituted with at least one polyalkylene oxide at the anomeric carbon of the polysaccharide.

Accordingly, it is an object of the present invention to provide novel diblock copolymers of polysaccharides and polyalkylene oxides.

It is another object of the present invention to provide oral hygiene non-food compositions containing the diblock copolymers as antiplaque or anticalculus agents.

A further object of the present invention is to provide antiplaque/anticalculus agents having significant activity and being derived from safe starting materials such as polysaccharides and polyalkylene oxides.

It is yet another object of the present invention to provide a method of eliminating or substantially reducing bacterial aggregation in an oral cavity or in an aqueous medium.

It is still another object of the invention to provide a method of preventing or substantially reducing bacterial aggregation or coaggregation in fermentation systems.

It is yet another object of the present invention to provide unique block copolymer that will function as effective dispersing agents for bacterial dispersions that would otherwise aggregate during storage.

These and other objects of the present invention will become more apparent in light of the detailed description and examples which follow.

SUMMARY OF THE INVENTION

The above objects are attained by the present invention which includes a block copolymer which contains at least one unit having a general formula I:

$$A\text{-}B \qquad (I)$$

wherein
A is a polysaccharide block,
B is a polyalkylene oxide block, and
B is linked to A at the anomeric carbon of A.

The inventive copolymers may be diblocks of formula AB, or triblocks of formulae ABA and BAB, (two anomeric carbons are required to produce a copolymer of Formula BAB), or polyblocks of formula $(AB)_n$. The inventive copolymers may contain pendant chains which may be an alkylene oxide or a saccharide, or any hydrophobic or charged group.

The present invention is based, in part, on the discovery that the inventive block copolymers inhibit bacterial aggregation whereas the individual blocks of polysaccharide and polyalkylene oxide as well as a physical combination of the two starting polymers are inactive.

The inventive compositions according to one preferred embodiment of the invention, which include the inventive block copolymers as active agents, inhibit adhesion and/or growth of bacteria responsible for dental plaque, thereby preventing the plaque formation, plaque-induced diseases, calculus formation, dental caries, gingivitis, and periodontal disease. The oral hygiene compositions of the present invention may be in the form of toothpastes, mouthwashes, rinses, tooth powders, gels, as well as other oral delivery non-food vehicles.

The invention also includes methods of inhibiting plaque formation and growth which include applying the inventive compositions into the oral cavity.

The inventive block copolymers are useful as active agents in any composition designed to prevent or reduce bacterial aggregation, build-up of biofilms, and biofouling in an aqueous system. In addition to oral hygiene compositions the inventive copolymers may be employed in water treatment systems and in fermentation processes and in the processing, storage, and distribution of bacterial dispersions. The inventive copolymers are also useful in dispersing bacterial aggregates.

DETAILED DESCRIPTION OF THE INVENTION

The present invention is based, in part, on the discovery of the novel block copolymers which contain at least one unit of Formula I:

$$A\text{-}B \qquad (I)$$

wherein A is a polysaccharide, i.e., at least disaccharide, and

B is polyalkylene oxide linked to the polysaccharide at the anomeric carbon of the polysaccharide.

Polysacharides suitable for use in the present invention must contain at least one reducing "sugar" or saccharide unit. Suitable polysaccharides may be linear or branched; suitable polysaccharides may comprise the same saccharide unit or may contain different saccharide units e.g., glucose, rabinose, xylose. Polysaccharides that are chemically modified are also suitable for use in the present invention. Examples of chemically modified saccharides are hydrophobic saccharides, cationic saccharides, anionic saccharides, hydrolyzed saccharides, oxidized saccharides and enzymatically treated saccharides.

The molecular weight of the polysaccharides suitable in the present invention generally does not exceed 1,000,000. Preferably, the molecular weight does not exceed 100,000 in order to ease the synthesis of inventive copolymers, although polysaccharides of any molecular weight are suitable as long as the polysaccharide is water-dispersible or water-soluble.

The preferred molecular weight of the Polysaccharides employed in the present invention is in the range of from 1,000 to 100,000, most preferably in the range of from 1,000 to 50,000 in order to maximize the ease with which the reaction may be conducted.

Suitable polysaccharides include but are not limited to dextran, starch, and modified starch, chitin, chitosan, modified chitosan, polyuronides, hyaluronic acid, starch hydrolyzates, (e.g., maltodextrins); modified celluloses, (e.g., carboxymethyl cellulose, hydroxyethyl cellulose, hydroxypropl cellulose, cellulose acetate); gums, (e.g., carrageenan, agar, xanthan, gum arabic, guar, gum tragacanth locust bean gum, pectins); modified gums, (e.g., hydrophobically modified and charged gums, e.g., modified guar and xanthan gum); hydrophobically modified polysaccharides, (e.g., hydrophobically modified hydroxyethyl cellulose); cationically modified polysaccharides (e.g., diethylaminoethyl dextran, cationically modified hydroxyethyl cellulose). Additional suitable gums are disclosed in BeMiller, J. N. "Gums Industrial" in Encyclopedia of Polymer Science and Engineering; John Wiley & Sons, Vol. 7, which is incorporated by reference herein. Additional suitable polysaccharides and gums are disclosed in Roy L. Whistler and James N. BeMiller, "Industrial Gums" 3rd Edition, 1993, which is incorporated by reference herein.

Polysaccharides suitable for use in the present invention are water-dispersible or water-soluble. Preferably, polysaccharides employed in the present invention are water-dispersible. The term "water-dispersible" as used herein means that the 0.1% (or preferably 1%) mixture of a polysaccharide in water does not macroscopically separate into two distinct phases at ambient temperature (20°–25° C.), although on a microscopic scale there are two distinct phases present. The term "water-soluble" as used herein means that the solubility of the particular material in water is at least 0.1%, more preferably at least 1%, at ambient temperature (20°–25° C.)

The suitable polysaccharides must be water-dispersible or water-soluble in order to make it possible for the inventive copolymer to attach to the surface of bacteria. The preferred polysaccharides are water-soluble.

Polyalkylene oxides suitable for use in the present invention are linear homo- or copolymers of ethylene oxide, or propylene oxide, or mixtures thereof, and may optionally contain small amounts of higher alkylene oxides such as butylene oxide. Polyalkylene oxide suitable for use in the present invention may or may not be endcapped. In the event that an endcapped polyalkylene oxide is used as described herein, the diblock of formula AB will predominantly result. In the event that a hydroxyterminated polyalkylene oxide (e.g., uncapped) is employed as described herein, a triblock of formula ABA or a polyblock of formula $(AB)_n$ is predominantly formed. Polyalkylene oxides suitable for use in the present invention are water-soluble in order to provide an optimal hydration barrier or a steric barrier which acts to keep the bacteria apart.

The molecular weight of the polyalkylene oxides suitable in the present invention generally does not exceed 50,000 and is generally in the range of from 350 to 50,000, preferably is in the range of from 1,000 to 30,000, most preferably in the range of from 1,000 to 20,000 although Polyalkylene oxide of any molecular weight is suitable as long as the polyalkylene oxide is water-soluble (i.e., at least 0.1% in water, preferably 1% in water, at ambient temperature).

When it is desired to obtain a diblock copolymer of formula AB according to the present invention, polyalkylene oxides are employed which are mono-endcapped with an alkoxy group, (e.g., methoxy or ethoxy or any alkoxy group, as long as the alkoxy group does not render the copolymer water-insoluble).

The inventive block copolymers are at least water-dispersible and preferably are water-soluble in order to maximize the efficacy of the copolymers in preventing bacterial aggregation. The molecular weight of the inventive block copolymers ranges generally from about 1,000 to about 1,000,000, preferably from about 1,000 to about 100,000, and optimally from 1,000 to 50,000, in order to ease the synthesis and optimize functional properties of the inventive copolymers.

The preferred block copolymers according to the present invention are represented by the following list: Dextran 6K-PEG 350; Dextran 6K-PEG 750; Dextran 6K-PEG 2000; Dextran 6K-PEG 5000; Dextran 40K-PEG 350; Dextran 40K-PEG 750; Dextran 40K-PEG 2000; Dextran 40K-PEG 5000; Dextran 110K-PEG 5000; Dextrin 10-PEG 350; Dextran 15-PEG 350; maltodextrin-PEG copolymers, and starch hydrolyzate-PEG copolymers. In the preceding sentence numbers refer to molecular weights and "PEG" stands for "polyethyleneglycol".

The above copolymers are preferred due to their maximum efficiency and ease of their synthesis.

According to the present invention, the method for preparation of the inventive copolymers includes several steps; the procedure being employed is typically used in the art whenever substitution at an anomeric carbon of saccharide is desired.

Any method which attains substitution at an anomeric carbon may be used. Known methods include direct glycosidation, transetherification, and other methods.

A method employed herein generally involves protection of the hydroxyl groups on a polysaccharide with selective activation of an anomeric carbon. The method is preferred in order to obtain highly selective substitution at the anomeric carbon. The protected activated polysaccharide is then reacted with a polyalkylene oxide to form an ether linkage. The last step involves the removal of the protective groups to give an inventive block copolymer. The method for substitution at an anomeric carbon of a saccharide is described generally in Whistler, R. L. and Wolfrom, M. L., Methods In Carbohydrate Chemistry, Vol. II, Sections [54], [55], [88], (1963).

A more detailed description of the preferred method for the preparation of the inventive block of polymers includes the following steps:

(a) protecting hydroxyl groups on a polysaccharide, preferably by esterifying with an anhydride or acid halide (e.g., acid chloride). Preferably, the esterification is carried out with an anhydride because the anhydride serves also as a solvent which in turn allows for easy removal of unreacted anhydride;

(b) selectively activating the anomeric carbon by deprotecting the hydroxyl group at the anomeric carbon. This step is carried out while keeping the protection of other hydroxyl group. This step is accomplished preferably by reacting with the phosphorous bromide;

(c) activating a polyalkylene oxide by reacting under inert atmosphere and in the dark the polyalkylene oxide and an oxidizing agent in the presence of a catalyst (preferably silver oxide/iodine) until the reaction is complete), typically for at least half an hour, preferably at least one hour. The amount of silver oxide employed is preferably in a slight excess (e.g., 1.1:1). The ratio of iodine to the polyalkylene oxide is preferably 0.2:1. In a preferred method, iodine is added after the polyalkylene oxide has been reacted with silver oxide for at least one hour;

(d) dissolving the protected activated polysaccharide obtained in step (b) in a suitable alcohol-free solvent (e.g., chloroform, acetone, methylene chloride);

(e) adding dropwise the solution resulting in step (d) to the polyalkylene oxide mixture obtained in step (c). The molar ratio of polysaccharide to polyalkylene oxide is 1:1 in order to obtain a diblock. The molar ratio is 2:1 to obtain a triblock ABA. The ratio is 1:2 in order to obtain a triblock BAB;

(f) reacting a mixture obtained in step (e) at room temperature for about 24 hours;

(g) deprotecting the resulting copolymer e.g., by reacting with sodium methoxide.

The inventive copolymers may be used whenever it is desirable to prevent or substantially reduce bacterial aggregation or coaggregation. According to the present invention, a method of inhibiting or reducing the bacterial aggregation includes applying an effective amount of at least one inventive block copolymer into a medium containing bacteria.

In one embodiment of the invention the inventive copolymers are included as an essential ingredient into oral hygiene non-food compositions. The oral hygiene compositions according to the invention include from 0.01% to 20%, preferably from 0.1% to 5% of the inventive copolymers. The inventive copolymers act as antiplaque and/or anticalculus agents by preventing bacterial aggregation in an oral cavity and thereby preventing plaque and/or calculus formation.

The preferred oral compositions of the present invention are in the form of toothpaste, dental cream, gel or tooth powder, as well as mouthwash, pre-brushing rinse, or post-brushing rinse formulations.

Ingredients typically included in toothpastes and gels may be used in toothpaste and gel compositions in accordance with the invention. Suitable ingredients include abrasive polishing materials, sudsing agents, flavoring agents, humectants, binders, sweetening agents, and water.

Mouthwashes are typically comprised of a water/alcohol solution, flavor, humectant, sweetener, foaming agent, and colorant.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Binders suitable for use in the compositions of the invention include hydroxyethyl cellulose (Natrosol®), sodium carboxymethyl cellulose and hydroxypropyl cellulose (Klucel®), as well as xanthan gums, Irish moss and gum tragacanth. Binders may be present in the toothpaste of the invention to the extent of from 0.01 to 10%. Sweeteners suitable for use in the present dentifrice, preferably at levels of about 0.1% to 5%, include saccharin.

Suitable foaming agents include soap, anionic, cationic, nonionic, amphoteric and/or zwitterionic surfactants. These may be present at levels of 0 to 15%, preferably 0.1 to 15%, more preferably 0.25 to 10% by weight. It should be noted that many of the glycoside-surface active agents described in the present invention also may be used as foaming agents at concentrations ranging from 0 to 15% by weight.

Certain pyrophosphate and other polyphosphate salts have been disclosed in U.S. Pat. Nos. 4,515,772 and 4,627,977 as being useful as anti-calculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Various anionic polymers may be employed as anticalculus and/or antiplaque agents. Suitable polymers include carboxylate polymers, sulfonate polymers, polymers containing a sulfonate and a carboxylate moiety, carboxylate polymers containing phosphonate units, and mixtures thereof. The carboxylate polymers suitable in the present compositions are described by Gaffar et al., U.S. Pat. No. 4,808,400, incorporated by reference herein. Suitable carboxylate polymers containing mono- or disubstituted hypophosphite units along the polymer backbone are described in a U.S. Pat. No. 5,011,682 incorporated by reference herein. The anionic polymers may be included at a level from about 0.01 to about 10%, preferably from about 0.05 to about 5%.

Zinc salts are disclosed as anti-calculus and anti-plaque agents in U.S. Pat. No. 4,100,269 and in U.S. Pat. Nos. 4,416,867, 4,425,325 and 4,339,432. Preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Flavors are usually included in toothpastes in low amounts, such as from 0.01 to about 5% by weight, especially from 0.1% to 5%.

Water-soluble antibacterial agents, such as chlorhexidine digluconate, hexetidine, alexidine, quaternary ammonium anti-bacterial compounds and water-soluble sources of certain metal ions such as zinc, copper, silver and stannous (e.g., zinc, copper and stannous chloride, and silver nitrate) may also be included.

Titanium dioxide is a suitable whitener.

Dyes/colorants suitable for dentifrices, i.e., FD&C Blue #1, FD&C Yellow #10, FD&C Red #40, etc., may be employed in the dentifrices of the invention.

Various other optional ingredients may be included in the compositions of the invention. Examples include, but are not limited to, preservatives, vitamins such as vitamin C and E, other anti-plaque agents such as stannous salts, copper salts, strontium salts and magnesium salts. Also included may be pH adjusting agents, anti-caries agents such as urea, calcium glycerophosphate, sodium trimetaphosphate, silicone polymers, plant extracts, desensitizing agents for sensitive teeth such as potassium nitrate and potassium citrate, and mixtures thereof.

Casein and/or its hydrolysate may be included as anticaries agents, e.g., at a level of 0.01 to 20% by weight, preferably 0.1 to 10%.

The corresponding compounds mentioned above which are used in toothpastes, are generally suitable within the ranges above for mouthwashes as well. The mouthwash can include ethanol at a level of from 0 to 60%, preferably from 5 to 30% by weight.

Further, the inventive block copolymers may be employed to prevent or substantially reduce bacterial aggregation or coaggregation in any aqueous medium. For example, in water towers (e.g., cooling towers, swimming pools, pipes, etc.), generally used at concentrations of from 0.01% to 20%.

The inventive copolymers may also be employed as deflocculating agents in fermentation systems, since such systems typically involve the presence of large amounts of bacteria.

The following specific examples further illustrate the invention, but the invention is not limited thereto.

EXAMPLE 1

Synthesis of Dextran-Methoxypolyethylene Glycol Diblocks (FIG. 2)

An example of the synthesis of a copolymer within the scope of the invention is as follows:

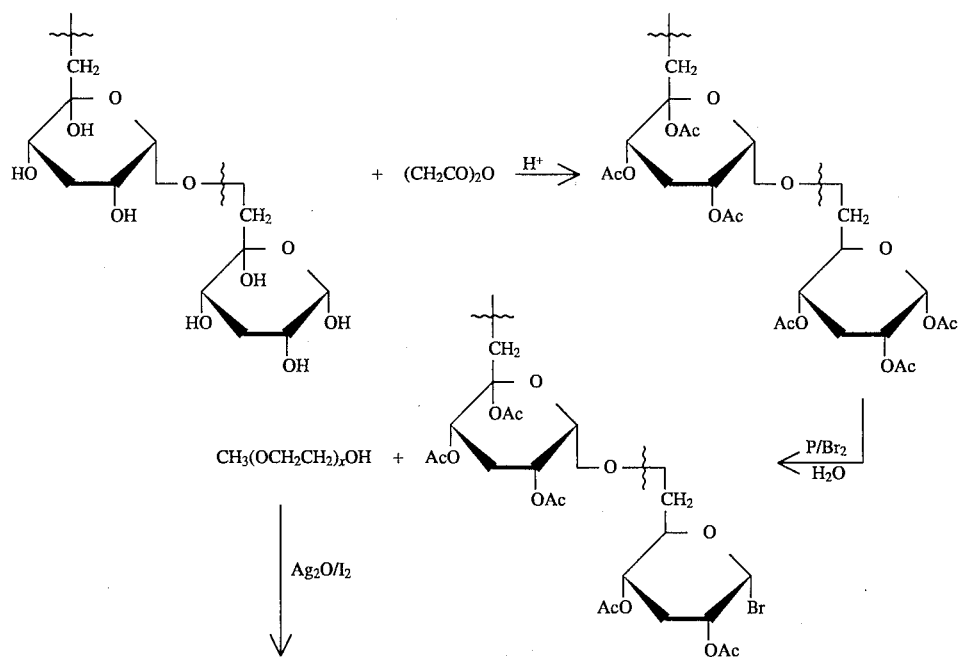

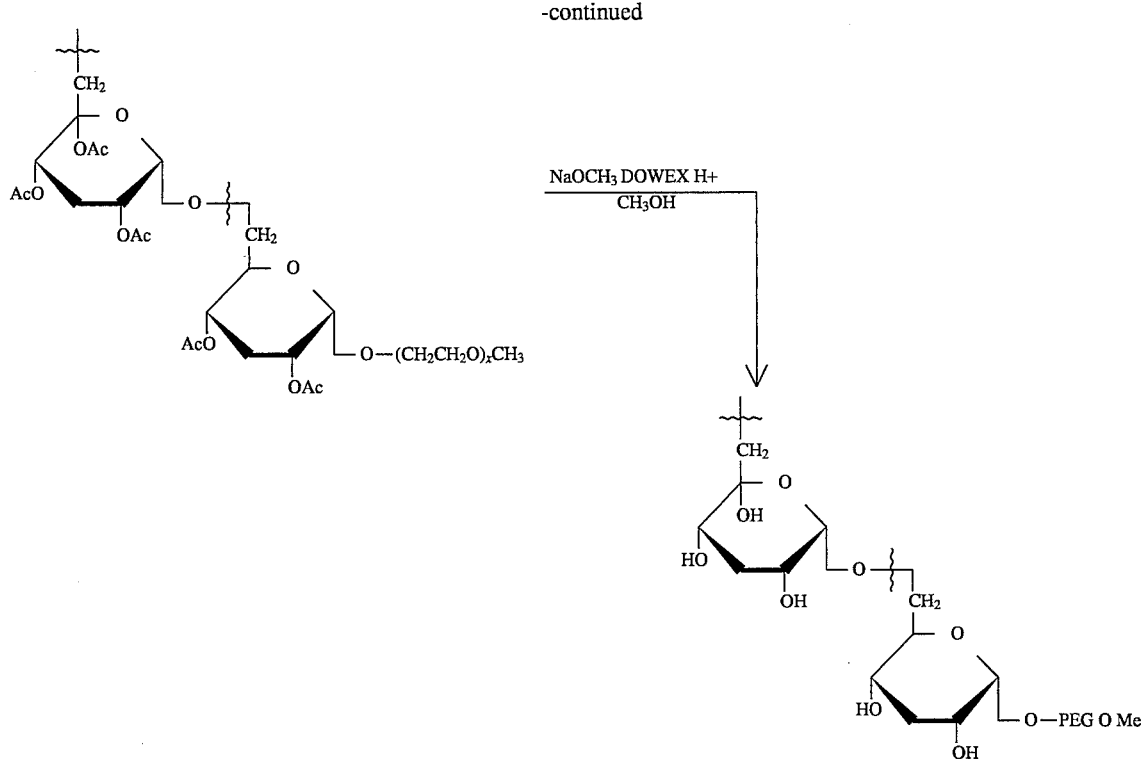

Synthesis of Acetobromodextran 200 ml of acetic anhydride (FW 102.09, b.p. 138°–140°, d. 1.082) were placed in a 500-ml three-necked flask equipped with a mechanical stirrer, a thermometer and an ice bath was added. Perchloric acid (60–70%, 1.2 ml) was added dropwise to the cold acetic anhydride. The ice-bath was removed and the mixture was allowed to warm to room temperature, then heated to 60°–70° C. 50 g of dextran (MW 6,000; $8.3 \times 10^{-3}$ moles monomer) was added in small portions over an hour, with vigorous stirring. When all dextran dissolved, the mixture was allowed to cool to room temperature. Red phosphorus (0.5 g, AW 30.97, $1.6 \times 10^{-2}$ moles) was added to the reaction mixture. Bromine (1 ml, MW 159.82, $1.9 \times 10^{-2}$ moles) was slowly added to the mixture followed by dropwise addition of water (0.6 ml, $3.3 \times 10^{-2}$ moles). The reaction was allowed to proceed at room temperature for 2 hours. Excess liquid was evaporated off under reduced pressure. The residue was suspended in 250 ml of a saturated sodium bicarbonate solution and filtered. The procedure was repeated until the filtrate becoame neutral. Final washes were carried out with water and the acetobromodextran was dried in a vacuum oven.

Glycosidation

Preparation of ethanol-free chloroform: Chloroform (300 ml) was extracted four times with 30 ml each of concentrated sulfuric acid. The chloroform was then washed successively with 50 ml each of water, saturated sodium bicarbonate solution and then with water. The chloroform was dried over sodium sulfate overnight and protected from light.

Monomethoxypolyethylene glycol (Carbowax 350, $5 \times 10^{-3}$ moles), silver oxide (1.3 g, FW 231.74, 99%, $5.5 \times 10^{-3}$ moles), predried Drierite (100 g) and the freshly prepared alcohol-free chloroform (100 ml) were placed in a 500-ml three-necked flask equipped with a mechanical stirrer, dry nitrogen feed and a 250-ml dropping funnel. The reaction flask was protected from light and the reaction mixture was allowed to stir for 1 hour at room temperature. Subsequently, iodine (0.25 g, FW 253.81, $1 \times 10^{-3}$ moles) was added. The acetobromodextran (51 g, Mr 10,197, $5 \times 10^{-3}$ moles) was dissolved in 150 ml of dry, alcohol-free chloroform and the resulting mixture (acetobromodextran in alcohol-free chloroform) was transferred to the dropping funnel. The reaction mixture (acetobromodextran and monomethoxypolyethylene glycol) was stirred for another 24 hours and filtered through a bed of fine glass wool. The glass wool bed was washed down thoroughly with chloroform. The chloroform layer was evaporated off under reduced pressure.

Deacetylation

The acetodextran-methoxypolyethylene glycol (20 g) was suspended in 200 ml of 0.05N sodium methoxide solution in methanol. The mixture was stirred at room temperature overnight. The reaction suspension was then stirred with about 15 g of dry Dowex 50W-W2 (5.1 meq/g dry resin) until an aliquot of the solution in water was neutral. The resin and crude product were removed by filtration. The solid was washed several times with methanol. The solid mixture was resuspended in water to dissolve the polymer product and the resin was filtered off. The filtrate was lyophilized to yield the diblock polymer.

EXAMPLE 2

Characterization of Dextran-Polyethylene Glycol (Dextran-PEG) Diblocks $H^1$ NMR was performed using a Varian XL300 Multinuclear spectrometer. Samples were dissolved in either deuterated dimethylsulfoxide or deuteriam oxide containing TMS. In deuterium oxide, the NMR spectra showed an anomeric proton at 5 ppm, the glycosidic ring protons between 3–4 ppm with a singlet at 3.7 ppm representing the methylene protons of the polyethylene glycol and a singlet around 3.4 ppm for the methoxy protons.

Solubility Study. The summary of several of the block copolymers synthesized as well as their water solubility are given in Table 1. The numbers in a copolymer name indicate the molecular weight of individual blocks employed in a synthesis.

TABLE 1

| BLOCK COPOLYMERS SYNTHESIZED | WATER SOLUBILITY (mg/ml) |
|---|---|
| Dextran 6K-PEG 350 | 16.6 |
| Dextran 6K-PEG 750 | 14.3 |
| Dextran 6K-PEG 2000 | 11.1 |
| Dextran 6K-PEG 5000 | 20.0 |
| Dextran 40K-PEG 350 | 16.7 |
| Dextran 40K-PEG 750 | 20.1 |
| Dextran 40K-PEG 2000 | 14.3 |
| Dextran 40K-PEG 5000 | 16.7 |
| Dextran 110K-PEG 5000 | 22.2 |
| Dextrin 10*-PEG 350 | 5.2 |
| Dextrin 15**-PEG 350 | 5.2 |

*Dextrin is a maize starch hydrolyzate. Dextrin 10 contains about 85% of pentasaccharides with the rest being higher molecular weight oligosaccharides. Dextrin 10 has a molecular weight of about 1,700.
**Dextrin 15 has a molecular weight of about 1,100. Dextrins were obtained from Fluka Chemicals.

Gel Permeation Chromatography. The experiments were performed on a Waters 590 GPC/ALC system (Waters/Millipore Corp., Melford, Mass.) coupled in parallel to a Viscotek Differential Viscometer, Model 100 (Viscotek Corp, Porter, Tex.). The columns used were four Ultrahydrogel columns (120, 250, 500 and 1,000 A°) with 0.1M sodium nitrate as the mobile phase and a model 490 Refractive Index detector at 30°. The block copolymers displayed a distinct elution volume different from both the starting polymers.

EXAMPLE 3

Agglutionation Study

A *S. sanguis* S34 suspension having an optical density (O.D.) of 1.5 per ml (1 ml) was added to a 1,000 ppm of a copolymer solution in an adherence buffer (1 ml) and mixed well. Initial reading of the optical density of the mixture was then taken. The suspension was allowed to stand undisturbed and subsequent readings of optical density were taken at 30-minute intervals up to 4 hours. The control consisted of 1 ml of the bacterial suspension and 1 ml of the adherence buffer. Experiments were also carried out with each of the starting polymers as well as a physical mixture of the starting polymers. The results that were obtained are summarized in Tables 2–6.

TABLE 2

*S. sanguis*

OPTICAL DENSITY

| Time (h) | Control | Dextran 6K PEG 350 | Dextran 6K-PEG 2000 | Dextran 6K-PEG 5000 |
|---|---|---|---|---|
| 0 | 0.54 | 0.90 | 1.1 | 1.1 |
| 0.5 | 0.48 | 0.91 | 1.1 | 1.1 |
| 1.0 | 0.32 | 0.88 | 1.1 | 1.2 |
| 1.5 | 0.21 | 0.87 | — | 1.2 |
| 2.0 | 0.14 | 0.85 | 1.1 | 1.1 |
| 2.5 | — | — | 1.1 | — |
| 3.0 | 0.084 | 0.82 | 1.0 | 1.1 |
| 3.5 | 0.075 | 0.76 | — | 1.1 |
| 4.0 | 0.058 | 0.72 | 1.0 | 1.1 |
| 4.5 | 0.053 | 0.69 | 0.98 | — |
| 5.0 | 0.045 | 0.66 | 0.95 | — |

TABLE 3

*S. sanguis*

OPTICAL DENSITY

| Time (h) | Control | Dextran 40K-PEG 350 | Dextran 40K-PEG 750 | Dextran 40K-PEG 2000 | Dextran 40K-PEG 5000 |
|---|---|---|---|---|---|
| 0 | 0.87 | 1.1 | 1.1 | 1.2 | 1.1 |
| 0.5 | 0.76 | 1.2 | 1.2 | 1.2 | 1.2 |
| 1.0 | 0.68 | 1.2 | 1.2 | 1.2 | 1.2 |
| 1.5 | 0.52 | 1.2 | 1.1 | 1.2 | 1.1 |
| 2.0 | 0.32 | 1.1 | 1.1 | 1.2 | 1.1 |
| 3.0 | 0.17 | 1.1 | 1.1 | 1.2 | 1.1 |
| 3.5 | 0.14 | 1.1 | 1.1 | 1.1 | 1.1 |
| 4.0 | 0.12 | 1.1 | 1.1 | 1.1 | 1.1 |

TABLE 4

*S. sanguis*

OPTICAL DENSITY

| Time (H) | Control | Dextrin 10-PEG 350 |
|---|---|---|
| 0 | 0.87 | 1.0 |
| 0.5 | 0.76 | 1.2 |
| 1.0 | 0.68 | 1.2 |
| 1.5 | 0.52 | 1.2 |
| 2.0 | 0.32 | 1.2 |
| 3.0 | 0.17 | 1.2 |
| 3.5 | 0.14 | 1.1 |

*Dextrin is a maize starch hydrolyzate consisting of about 89% of pentasaccharides with the rest being higher molecular weight oligosaccharides. Dextrin 10 has a molecular weight of about 1,700.

TABLE 5

*S. mutans*

OPTICAL DENSITY

| Time (h) | Control | Dextran 6K-PEG 350 | Dextran 6K-PEG 2000 | Dextran 6K-PEG 5000 |
|---|---|---|---|---|
| 0 | 0.99 | 1.2 | 1.1 | 1.2 |
| 0.25 | 0.98 | 1.2 | 1.2 | 1.2 |
| 0.50 | 0.97 | 1.2 | 1.2 | 1.2 |
| 1.0 | 0.96 | 1.2 | 1.2 | 1.2 |
| 1.5 | 0.95 | 1.2 | 1.2 | 1.2 |
| 2.0 | 0.3 | 1.2 | 1.2 | 1.2 |
| 2.5 | 0.91 | 1.2 | 1.2 | 1.2 |
| 3.0 | 0.89 | 1.2 | 1.2 | 1.2 |
| 3.5 | 0.88 | 1.2 | 1.2 | 1.2 |
| 4.0 | 0.87 | 1.2 | 1.2 | 1.2 |

TABLE 6

S. mutans

| Time (h) | Control | OPTICAL DENSITY | | | |
|---|---|---|---|---|---|
| | | Dextran 40K- PEG 350 | Dextran 40K- PEG 750 | Dextran 40K- PEG 2000 | Dextran 40K- PEG 5000 |
| 0 | 0.99 | 1.2 | 1.2 | 1.2 | 1.2 |
| 0.25 | 0.98 | 1.2 | 1.2 | 1.2 | 1.2 |
| 0.5 | 0.97 | 1.2 | 1.2 | 1.2 | 1.2 |
| 1.0 | 0.96 | 1.2 | 1.2 | 1.2 | 1.2 |
| 1.5 | 0.95 | 1.2 | 1.2 | 1.2 | 1.2 |
| 2.0 | 0.93 | 1.2 | 1.2 | 1.2 | 1.2 |
| 2.5 | 0.91 | 1.2 | 1.2 | 1.2 | 1.2 |
| 3.0 | 0.89 | 1.2 | 1.2 | 1.2 | 1.2 |
| 3.5 | 0.88 | 1.2 | 1.2 | 1.2 | 1.1 |
| 4.0 | 0.87 | 1.2 | 1.2 | 1.2 | 1.1 |

A very well dispersed microbial suspension is indicated by the higher value in optical density. Self-aggregation of bacteria can be detected by the drop in optical density after time 0. Hence, the higher the optical density, the less microbial aggregation. It is clear that S. sanguis tends to autoaggregate as seen in the rapid drop of the optical density with time whereas S. mutans does not. In the case of S. sanguis, the inventive block copolymerss not only increased the initial dispersion of the bacteria but effectively kept the bacteria well dispersed throughout the length of the experiment. In the case of S. mutans, the block copolymers effectively facilitated further dispersion of the bacteria.

In every case, the block copolymer within the scope of the invention totally prevented the bacterial self-aggregation all the way up to at least 4 hours. This is indicated by the constant optical density of the bacterial suspension from time 0 to time 4 hours. In fact, the block copolymers help disperse the suspension as evidenced by the increase in the optical density from time 0 to time 0.5 h. On the other hand, the control shows a drop in the optical density (indication of aggregation) from time 0. At the end of the 4 hour interval, most of the bacteria had aggregated and dropped out of solution as seen in a drastic drop in the optical density to 0.2–0.1. The starting dextran, regardless of molecular weight, had no effect on the bacterial aggregation. Neither did the methoxy- polyethylene glycol or the physical combination of dextran and polyethylene glycol. This is indicated by the bacterial aggregation which, in spite of the presence of the polymer, still occurred in a similar fashion as for the control.

A comparison of data obtained with control at time 0 with data obtained at time 0 in samples where an inventive copolymer is added to a control shows that the inventive copolymers disperse effectively an already formed bacterial aggregate.

EXAMPLE 7

A typical toothpaste formula containing the block copolymer plaque inhibitor of the present invention is as follows:

| Toothpaste Formula (pH = 5–9) | |
|---|---|
| COMPONENT | PERCENT BY WEIGHT OF THE FINAL COMPOSITION |
| 70% Sorbitol | 64.0% |
| Abrasive Silica | 10.0% |
| Thickening Silica | 9.0% |
| Block Copolymer Antiplaque Agent | 5.0% |
| Polyethylene Glycol | 5.0% |
| Sodium Dodecyl Sulfate | 1.5% |
| 5-chloro-2-(2,4-dichloro-phenoxyphenol) | 0.25% |
| Flavor | 1.0% |
| Sodium Saccharinate | 0.3% |
| Sodium Fluoride | 0.24% |
| Preservative (Benzoate) | 0.08% |
| Dye | <.01% |
| Sodium Carboxymethyl Cellulose | 0.15% |
| Water | to 100% |

Substantially similar formulae but including additional antitartar agent such as Gantrez® resins (ISP Inc.), and/or pyrophospate may also be formulated.

EXAMPLE 8

A typical formula for a mouthwash containing the block copolymer agent of the present invention is as follows:

| Mouthwash Formula (pH = 6.5) | |
|---|---|
| COMPONENT | PERCENT BY WEIGHT OF FINAL COMPOSITION |
| Ethanol | 12.5% |
| 70% Sorbitol | 7.0% |
| Block Copolymer Anti-plaque Agent | 5.0% |
| Tween 20 ® | 0.55% |
| Preservatives (parabens) | 0.2% |
| Flavor | 0.1% |
| Dye | <.1% |
| Sodium Saccharinate | 0.65% |
| Sodium Chloride | 0.05% |
| Sodium Acetate | 0.015% |
| Acetic Acid | 0.015% |
| Water | to 100% |

The ingredients included in the Examples may be obtained from the following suppliers: Dextrans and Dextrins were obtained from Fluka Chemicals; polyethylene glycols were obtained from Union Carbide. All other chemicals were obtained from Aldrich. Dowex 50W-W2 is an ion exchange resin from Aldrich.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A block copolymer comprising at least one unit of a general formula I:

$$A-B \qquad (I)$$

wherein

A is a polysaccharide block,

B is a polyalkylene oxide block, and

B is covalently bound to A solely at the anomeric carbon of A.

2. The copolymer of claim 1 wherein B is mono-end-capped with an alkoxy group.

3. The copolymer of claim 1 wherein the B is selected from the group consisting of polypropylene glycol, polyethylene glycol, 1-alkoxypolyethylene glycol, and 1-alkoxypolypropylene glycol.

4. The copolymer of claim 1 wherein the molecular weight of A is in the range of from about 1,000 to about 1,000,000 as determined by gel permeation chromatography.

5. The copolymer of claim 1 wherein the molecular weight of B is in the range of from about 350 to about 50,000 as determined by gel permeation chromatography.

6. The copolymer of claim 1 wherein A is a dextran.

7. The copoymer of claim 2 wherein B is 1-alkoxypolyethylene glycol.

8. The copolymer of claim 7 wherein A is dextran.

9. The copolymer of claim 1 wherein the molecular weight of copolymer ranges from about 1,000 to about 1,000,000 as determined by gel permeation chromatography.

10. The copolymer of claim 1 wherein B is water soluble.

11. An oral hygiene non-food composition comprising (a) the copolymer of claim 1 in an effective amount to reduce or eliminate bacterial aggregation in an oral cavity; and (b) a pharmaceutically acceptable carrier in an effective amount to deliver the copolymer into the oral cavity.

12. The composition of claim 10 wherein the the copolymer of claim 1 is present in the amount of from 0.01% to 20%, by weight of the composition.

13. A method of preventing bacterial aggregation in an oral cavity by applying into the oral cavity the copolymer of claim 1.

14. A method of preventing bacterial aggregation in an oral cavity by applying into the oral cavity the composition of claim 7.

15. A method of preventing bacterial aggregation in an aqueous system, the method comprising introducing into the aqueous system the copolymer of claim 1.

16. A method of dispersing a bacterial aggregate by treating the aggregate with the copolymer of claim 1.

17. The copolymer of claim 1 wherein the copolymer is water-soluble or water dispersible.

* * * * *